US008840557B2

(12) United States Patent
Casciaro et al.

(10) Patent No.: US 8,840,557 B2
(45) Date of Patent: Sep. 23, 2014

(54) ULTRASONIC APPARATUS FOR MEASURING A LABOR PROGRESS PARAMETER

(75) Inventors: Sergio Casciaro, Lecce (IT); Ernesto Casciaro, Lecce (IT); Francesco Conversano, Monopoli (IT)

(73) Assignee: CNR—Consiglio Nazionale delle Ricerche, Rome (IT)

( * ) Notice: Subject to any disclaimer, the term of this patent is extended or adjusted under 35 U.S.C. 154(b) by 434 days.

(21) Appl. No.: 13/129,263

(22) PCT Filed: Nov. 23, 2009

(86) PCT No.: PCT/EP2009/008321
§ 371 (c)(1),
(2), (4) Date: Jun. 2, 2011

(87) PCT Pub. No.: WO2010/057665
PCT Pub. Date: May 27, 2010

(65) Prior Publication Data
US 2011/0257529 A1    Oct. 20, 2011

(30) Foreign Application Priority Data

Nov. 21, 2008  (IT) .............................. PI2008A0118

(51) Int. Cl.
*A61B 8/00* (2006.01)
*A61B 8/08* (2006.01)
*A61B 5/107* (2006.01)

(52) U.S. Cl.
CPC ............. *A61B 8/0866* (2013.01); *A61B 8/5223* (2013.01); *A61B 5/1076* (2013.01); *A61B 8/4209* (2013.01); *A61B 8/463* (2013.01); *A61B 8/469* (2013.01)
USPC ............................. 600/443; 600/437; 600/407

(58) Field of Classification Search
USPC .................. 600/443, 313, 338, 344, 376, 453
See application file for complete search history.

(56) References Cited

U.S. PATENT DOCUMENTS

5,787,889 A * 8/1998 Edwards et al. .............. 600/443
6,270,458 B1 * 8/2001 Barnea .......................... 600/438
(Continued)

*Primary Examiner* — Tse Chen
*Assistant Examiner* — Joel F Brutus
(74) *Attorney, Agent, or Firm* — R. Ruschena Patent Agent, LLC (57) ABSTRACT

An apparatus (10) for measuring one or more labor progress parameters (25) as the dilation of the endocervical canal (8), the rotation and the position of the head (4) of the foetus (3) during the descent, the duration and the intensity of the uterine contractions, other morphological and physiological parameters, without introducing foreign objects into the body of a pregnant woman (2) and independently from the sensitivity of the operator. The apparatus (10) comprises automatic means for tracking, in a sequence of ultrasound images (11, 12) that are obtained by an ultrasound probe (1), one or more regions of interest (ROI, 21), that may be both two-dimensional or three-dimensional and are centered about anatomic reference points (28) that define said parameters selected in a reference image by a displaying unit (14). The tracking means comprises: a) a means for calculating a function (f) at the pixels of the ROI of the reference image and of images preferably sampled among the images of the sequence, b) a means for calculating iteratively at the positions of the ROI in subsequent images, by a means of comparison between the values of the function (f) calculated in the pixels of the ROI of a current image and the values of the function (f) calculated in the pixels of the ROI of a subsequent ultrasound image; c) a means for comparing each position of the ROI with the position of the ROI in the reference image and for calculating the labor progress parameter responsive to said comparison. The new position of the region of interest may be defined as a domain in which a predetermined object function assumes a minimum value.

14 Claims, 5 Drawing Sheets

(56) References Cited

U.S. PATENT DOCUMENTS

| | | | |
|---|---|---|---|
| 2002/0169378 A1* | 11/2002 | Mo et al. | 600/437 |
| 2003/0114779 A1* | 6/2003 | Paltieli | 600/588 |
| 2005/0226533 A1* | 10/2005 | Sandoz et al. | 382/287 |
| 2006/0058650 A1* | 3/2006 | Sharony | 600/437 |
| 2006/0282019 A1* | 12/2006 | Hamilton | 600/591 |
| 2008/0167581 A1 | 7/2008 | Paltieli | |
| 2009/0093716 A1* | 4/2009 | Deischinger et al. | 600/443 |

* cited by examiner

ULTRASONIC APPARATUS FOR MEASURING A LABOR PROGRESS PARAMETER

FIELD OF THE INVENTION

The present invention relates to an ultrasound-based apparatus for monitoring one or more morphological and physiological parameters that are related to the progress of a childbirth.

BACKGROUND OF THE INVENTION

A need is particularly felt of a method and an equipment that allow to monitor the conditions of a pregnant woman and her foetus before entering the childbirth room, and during the childbirth itself, in particular in childbirth stage 2 but even in stage 1 and 3. In particular, it is important to monitor such morphological and physiological parameters as uterine contractions intensity, frequency and duration, foetal cardiac frequency, endocervical canal dilation, endocervical canal length, foetal head station, in particular the distance of the foetal head from an anatomical reference, such as a parturient's bone, pubis, and the like, as well as the foetal head rotation, umbilical cord unwinding, and the evolution of all these parameters.

Various techniques are known for evaluating the imminence of the childbirth, and monitoring the childbirth progress. These methods provide the introduction of an operator's finger and/or such objects as sensors and/or instruments into the vagina, to reach the uterine cervix or the head of the foetus. These invasive techniques may also lead to infections and/or lesions of the parturient and/or the foetus.

Furthermore, in most cases the accuracy of the data that can be obtained depend upon the operator's sensitivity, therefore objectivity and precision of the measurement cannot be guaranteed. To cope with this problem, ultrasound devices have been developed such as the Barnev's cervicometer, described in Sharf et al., "Continuous monitoring cervical dilation and foetal head station during labor" (Med. Eng. Phys. 2007; 29:61-71). Barney's cervicometer comprises three ultrasound transmitters to be located on the abdomen of the pregnant woman, and a plurality of receivers to be located, typically, on the foetal head and at the edges of the cervical os. The analysis of the response time of the waves, and a subsequent triangulation of the distance obtained this way, allow to univocally evaluate the endocervical canal dilation and the foetus position. However, this device is still an invasive one, as well as the devices and the methods described in Shari et al., "Continuous monitoring cervical dilation and foetal reaction during labor" Medical Engineering & Physics 29 (2007) 61-71, in "Novel technologies for minimally invasive therapies", Lupensis Biomedical Publications, as well as in WO199849942, WO2008084486 and WO2005015499. Apart from the nuisance they can cause to the pregnant woman, these techniques can only be employed if the pregnant woman keeps a lying-down position.

Furthermore, the operator must hold the ultrasound probe and continually adjust its position on the woman's abdomen.

Moreover, only a limited number of parameters can be displayed and monitored at the same time, normally no more than two, by means of known equipment.

SUMMARY OF THE INVENTION

It is therefore an object of the invention to provide an apparatus for measuring morphological parameters that allow monitoring the progress of a labor, such as, in particular, the endocervical canal dilation of a parturient, the position of the foetus before and during the descent through the endocervical canal, as well as physiological parameters of the parturient and of the foetus, without requiring the introduction of any foreign matter into the pregnant woman's body.

It is, furthermore, an object of the invention to provide an apparatus for real-time monitoring such parameters, by qualitatively and/or quantitatively displaying them on a user interface.

It is another object of the invention to provide an apparatus that allows automatic measurement of such parameters.

It is still an object of the invention to provide an apparatus that allows objectively measuring such parameters, i.e. independently from the sensitivity and the skills of the operator.

It is a particular object of the invention to provide such an apparatus for monitoring at the same time a number of morphological and physiological parameters as desired by the operator.

It is a further particular object of the invention to provide such an apparatus that allows the parturient to assume any desired position during the childbirth, for example a standing or a sitting position, as well as a lying-down position.

These and other objects are achieved through an apparatus for measuring a labor progress parameter during childbirth by ultrasound images obtained by ultrasonic pulses, the apparatus comprising:

an ultrasound probe;

a fastening means for fastening the ultrasound probe onto a parturient's body so that the probe has a visual field that includes a portion of the parturient's body and of a foetus, in particular the parturient's endocervical canal and/or the pubis;

a control unit for receiving and analysing signals from the ultrasound probe, said control unit creating or receiving as input by said probe a reference ultrasound image and a plurality of subsequent ultrasound images, which are taken in succession after the reference ultrasound image;

a user interface for selecting a region of interest in the reference ultrasound image by an operator, the user interface adapted to select the region of interest substantially centred about the portion of the parturient's body, the region of interest comprising a plurality of pixels.

The main feature of the apparatus is that the control unit comprises:

an automatic tracking means for tracking the region of interest, said automatic tracking means adapted to identify respective derived regions of interest in selected images of the plurality of subsequent ultrasound images, the derived regions of interest deriving from the region of interest that is selected in the reference ultrasound image, the tracking means comprising:

a means for calculating a predetermined local pixel function for each pixel or group of pixels of the region of interest in the reference ultrasound image and in each selected image of the plurality of subsequent ultrasound images, a means for iteratively calculating, starting from the reference ultrasound image, the position of the derived region of interest in each selected image, the means for iteratively calculating adapted to perform comparisons between:

values of the local pixel function calculated at the pixels of the region of interest of an image of the selected images;

values of the local pixel function calculated at pixels of the region of interest of a subsequent ultrasound image;

a means for comparing each position of the derived regions of interest with the position of the region of interest in the reference ultrasound image or of In another image and for calculating a labor progress parameter, in particular of a previous image.

The automatic tracking means allow to track, substantially in real time and with a predetermined level of accuracy, before and during the childbirth, one or more morphological and physiological labor parameters that are related with the progress of the childbirth, and that allow evaluating the correct evolution of the childbirth itself, without inserting in the parturient's body foreign objects, such as intrusive instruments and sensors.

Furthermore, the device is adapted to integrate existing ultrasound instruments.

Advantageously, the control unit is adapted to select a further region of interest that is substantially centred about the portion of the parturient's body, the labor progress parameter during childbirth defined by a combination of the region of interest and of the further region of interest. This way, the parameter is totally defined without any reference to reference points external to the parturient's body or the foetus, and the tracking of the regions of interest is more reliable, in particular it is independent from movements of the parturient. The same do not apply to the case of one anatomic reference point only, even if the position of the probe with respect to an absolute coordinate system is known to the control unit. In this case, a point of the probe itself provides the second reference, which is needed to define together with the anatomic point a distance parameter or a line which defines an angle parameter.

Advantageously, the user interface is adapted to provide to the operator an option of selecting a further reference image among one of the subsequent ultrasound images, such that a first and a second tracking on two pluralities of pixels are carried out contemporaneously, the means for iteratively calculating adapted to perform the steps of:

comparing values of the local pixel function calculated at pixels of the region of interest of the reference ultrasound image, and values of the local pixel function calculated at pixels of the region of interest of a subsequent ultrasound image, such that a first position of the derived region of interest is identified;

comparing between values of the local pixel function calculated at pixels of the further reference image, and values of the local pixel function calculated at pixels of the region of interest of a subsequent ultrasound image, such that a second position of the derived region of interest is identified;

identifying a further derived region of interest through a comparison between the trackings of the first and the second positions of the derived region of interest according to a prefixed criterion.

This way, with the first tracking it is possible to take into maximum account any possible change of the tissues during the childbirth, whereas with the second tracking it is possible to eliminate artifacts that may affect the calculation of the derived region of interest.

Advantageously, the user interface is adapted to provide to said operator an option of selecting the criterion for carrying out the comparison between the first and the second tracking.

Preferably, such criterion is selected from the group comprised of:

the position that is identified by the lowest object function value;

the position that is closer to a predetermined set of values;

the position that is farther from a predetermined set of values;

an average position between the first and the second position.

In particular, the portions of the mother's body and of the child that are included in the visual field of the probe are those portions that markedly change their configuration and their position during the childbirth, in particular the edges of the external os and the head of the foetus; furthermore, portions of the foetus may be included in the visual field, for example the shoulders, which provide an absolute reference for evaluating the rotation of the head.

The regions of interest may be used for automatically tracking one of the moving portions in the images that follows the reference image, in terms of position with respect to portions of the woman's body that remains substantially fixed during the childbirth, for example the head of the foetus with respect to the pelvis.

Preferably, the apparatus comprises a means for measuring a position parameter of the ultrasound probe with respect to a coordinate system external to the parturient, and the control unit has a means for receiving the position parameter and a means for summing said position parameter and the position of said derived region of interest with respect to said probe, such that said means for comparing performs a comparison between the actual position of said regions of interest taking into account said coordinate system external to said parturient.

This way, an alignment is possible between the position of the region of interest in the reference image, and of the corresponding regions of interest on the subsequent images, and an univocal coordinate system, external to the woman's body, in particular a fixed coordinate system, in order to take into account the movements of the woman during the childbirth, more precisely during the time since the reference image is taken until the subsequent images are elaborated.

In particular the user interface is adapted to define as input a plurality of regions of interest selected by an operator on the reference image.

In particular, each region of interest defines a same labor progress parameter.

The labor progress parameter defined by the selected region of interest may be the dilation of the parturient's endocervical canal, which may be associated to a distance between two regions of interest selected on the edge of the endocervical canal.

The labor progress parameter defined by the selected region of interest may be the position of the head of the foetus during the descent along the outlet path through the endocervical canal, i.e. the "foetal head station"; the position may be associated with a region of interest that is selected on a fixed portion of the parturient's body and with a region of interest that is selected on the head of the foetus. In particular, the fixed portion of the parturient's body may be the pubis.

The labor progress parameter defined by the region of interest may be the rotation of the head of the foetus, i.e. the "foetal head position"; the rotation is then associated with an angle that is formed by a line that is defined by two regions of interest that are centred on a fixed portion of the parturient's body and by a line that is defined by two regions of interest integral to the foetus.

This way, the system allows reading all the physiological parameters of the foetus and of the parturient during the childbirth, in particular vital parameters by which the safety conditions for the foetus and the parturient can be monitored.

Reliable measures of this angle may be obtained by having as a reference the only the line that is defined by two regions of interest of the foetus.

In particular, the length of the endocervical canal is evaluated by measuring the dilation of an upper part and the dilation of a lower part of the endocervical canal, a computing means calculating the length by comparing the dilation of the upper part and of the dilation of the lower part.

In particular the ultrasound reference image and/or the subsequent ultrasound images are images of any cross sectional plane of the visual field selected by the operator.

Preferably, the region of interest is a region of a three-dimensional space.

In particular, the region of interest is a three-dimensional region that is directly obtained through a 3D real time or native matricial acquisition.

In alternative, the region of interest may be obtained as an union of regions of interest of a plurality of ultrasound images of plane sections of the visual field, wherein the plurality of reference images are obtained by rotating the visual field about an axis that is common to the plane sections.

The technique of reconstructing three-dimensional images starting from two-dimensional images reduces the calculations that are needed to obtain the reference three-dimensional image, with respect to the case of a direct acquisition of a volumetric image, i.e. a 3D-image.

Advantageously, the means for iteratively calculating positions of the region of interest comprises:

a means for calculating the local pixel function in a plurality of domains of the subsequent ultrasound images;

a means for calculating a predetermined object function in each of the domains, the object function associating to each domain a deviation value between the local pixel function as calculated in the domain and the local pixel function as calculated in the region of interest;

a means for determining a domain of a subsequent ultrasound image in which the object function has a minimum value.

Preferably, the object function is the sum of the square of the differences between a value of the local pixel function as calculated at each pixel of the region of interest of an ultrasound image, and the value of the local pixel function as calculated at each corresponding pixel in a domain of a subsequent ultrasound image, which may not immediately follow the reference image.

Advantageously, the images of the plurality of subsequent images in which the derived region is identified are selected by sampling at a predetermined frequency.

Preferably, the position of the head of the foetus is associated with a further region of interest that is selected on a fixed portion of the parturient's body and/or with a further region of interest that is selected at the head of the foetus.

For example, the local pixel function is a function that associates to a number each pixel of the region of interest and of the domains. In particular, the number that is associated by the local pixel function to a pixel may be related to a grey tonality of a grey scale. In alternative, such number may be a value that is deduced by a radiofrequency spectral analysis of an ultrasound image. In alternative, but not exclusively, such number may deduced by an analytic technique that is different from radiofrequency spectral analysis.

Preferably, the user interface provides a means for signalling an anomalous value of a labor progress parameter or of a phoetus physiological parameter with respect to a predetermined range, or an anomalous combination of a plurality of labor progress parameters and/or of physiological parameters.

Such anomalous values may represent a condition that is dangerous for the foetus and/or for the mother, with consequent risks for the onset of critical and potentially harmful configurations.

Preferably, the apparatus comprises a means for storing values of the labor progress parameters, in particular the anomalous value and the anomalous combination of values. This way, an off-line consultation of the childbirth history is possible, which is useful in case of doubts concerning the correct application of a safety procedure or of a good childbirth practice by a medical team, in particular, in case of unexpected complications that may have occurred during the childbirth. In some cases, for instance, the uterine contractions are not followed by cervix dilation, which causes foetal suffering; this is normally overcome by Caesarean section. The apparatus according to the invention enables the medical team to evaluate on an objective basis whether a Caesarean section is necessary, and to support by documentary evidence the need of such a practice.

An anomalous parameter value may also be generated that is far away from a physically acceptable range of parameter values, which requires checking equipment reliability, and/or resetting the means for calculating and/or starting again the calculations.

Advantageously, the apparatus comprises a means for displaying the parameter on the ultrasound images. A simplified image of the portions of the parturient's genital and reproductive system, as well as of the foetus, may be useful for evaluating the progression stage and the correct evolution of the childbirth. The numeric values of monitored parameters and/or of physiological data and/or of other useful parameters or images of various types measured with compatible devices may usefully accompany the ultrasound images on a same user interface or on a separate interface.

The aforementioned objects are still achieved through an ultrasound-based method for measuring a labor progress parameter, the method providing the steps of:

fastening an ultrasound probe onto the body of a parturient so that the probe has a visual field that includes a portion of the parturient's body and of a foetus, in particular the parturient's endocervical canal and/or the pubis;

providing a control unit for receiving and analysing signals from the ultrasound probe, creating or receiving as input by said probe a reference ultrasound image and a plurality of subsequent ultrasound images, which are taken in succession after the reference ultrasound image;

selecting through a user interface at least one region of interest in the reference ultrasound image, the region of interest substantially centred about the portion of the parturient's body, the region of interest comprising a plurality of pixels;

automatic tracking the region of interest and identifying respective derived regions of interest in selected images of the plurality of subsequent ultrasound images, the derived regions of interests corresponding to the region of interest that is selected in the reference ultrasound image, the tracking step comprising in turn the steps of:

calculating a predetermined local pixel function for each pixel or group of pixels of the region of interest of the reference ultrasound image and in each selected image of the plurality of subsequent ultrasound images, iteratively calculating, starting from the reference ultrasound image, the position of the derived region of interest in each selected image, and carrying out a comparison between:

values of the local pixel function calculated at the pixels of the region of interest of an image of the selected images;

values of the local pixel function calculated at pixel of the region of interest of a subsequent ultrasound image;

comparing each position of the derived region of interest with the position of the region of interest in the reference ultrasound image and calculating a labor progress parameter, in particular of a previous image.

Advantageously, a step is provided of selecting at least a further region of interest that is substantially centred about said portion of the parturient's body, the labor progress parameter during childbirth defined by a combination of the region of interest and of the further region of interest.

Advantageously, a step is provided of selecting by the operator a further reference image among one of the subsequent ultrasound images, such that a first and a second tracking on two pluralities of pixels are carried out contemporaneously; in this case, further steps are provided of:

comparing values of the local pixel function calculated at pixels of the region of interest of the reference ultrasound image, and values of the local pixel function calculated at pixels of the region of interest of a subsequent ultrasound image, such that a first position of the derived region of interest is identified;

comparing between values of the local pixel function calculated at pixels of the further reference image, and values of the local pixel function calculated at pixels of the region of interest of a subsequent ultrasound image, such that a second position of the derived region of interest is identified;

identifying a further derived region of interest through a comparison between the trackings of the first and the second positions of the derived region of interest according to a prefixed criterion.

Advantageously, a step is provided of selecting the above-mentioned criterion, which is selected, in particular, from the group comprised of:

an average position between the first ad the second position;

the position that is identified by the lowest object function value;

the position that is closer to a predetermined set of values;

the position that is farther from a predetermined set of values.

Preferably, further steps are provided of:

measuring a position parameter of the ultrasound probe with respect to a coordinate system external to the parturient, summing the position parameter and the position of the derived region of interest with respect to the probe, such that the means for comparing performs a comparison between the actual position of the regions of interest taking into account the coordinate system external to the parturient.

In particular, the step of receiving and analysing signals provides:

receiving a plurality of 2-D ultrasound images that are obtained by rotating the visual field about an axis that is common to the plane sections along which respective 2-D image extends;

joining together said 2-D images such that a 3-D ultrasound image is reconstructed, and such that a 3-D region of interest, i.e. a region of interest of a three-dimensional space, is also reconstructed.

Advantageously, the step of iteratively calculating positions of the region of interest provides:

calculating the local pixel function in a plurality of domains of the subsequent ultrasound images;

calculating a predetermined object function in each of the domains, the object function associating to each domain a deviation value between the local pixel function as calculated in the domain and the local pixel function as calculated in the region of interest;

determining a domain of the subsequent ultrasound image in which the object function has a minimum value.

Preferably, the object function is the sum of the squares of the differences between a value of the local pixel function as calculated at each pixel of the region of interest of an ultrasound image, and the value of the local pixel function as calculated in a domain of a subsequent ultrasound image, which may not immediately follow the reference image.

Advantageously, a step is provided of selecting the images in which the derived region is identified from the plurality of subsequent ultrasound images by sampling at a predetermined frequency.

The use of the procedure may be continuous or intermittent, responsive to the childbirth stage and to monitoring needs.

Preferably, the position of the head of the foetus is associated with a further region of interest that is selected on a fixed portion of the parturient's body and/or with a further region of interest that is selected on the head of the foetus.

Preferably, the method provides a step of signalling an anomalous value of a labor progress parameter with respect to a predetermined range, or an anomalous combination of a plurality of the labor progress parameters.

Preferably, the method provides a step of storing values of the labor progress parameters, in particular the anomalous value and the anomalous combination of values.

BRIEF DESCRIPTION OF THE DRAWINGS

The invention will now be shown with the following description of an exemplary embodiment thereof, exemplifying but not limitative, with reference to the attached drawings, in which.

DESCRIPTION OF PREFERRED EXEMPLARY EMBODIMENTS

Figure 5:
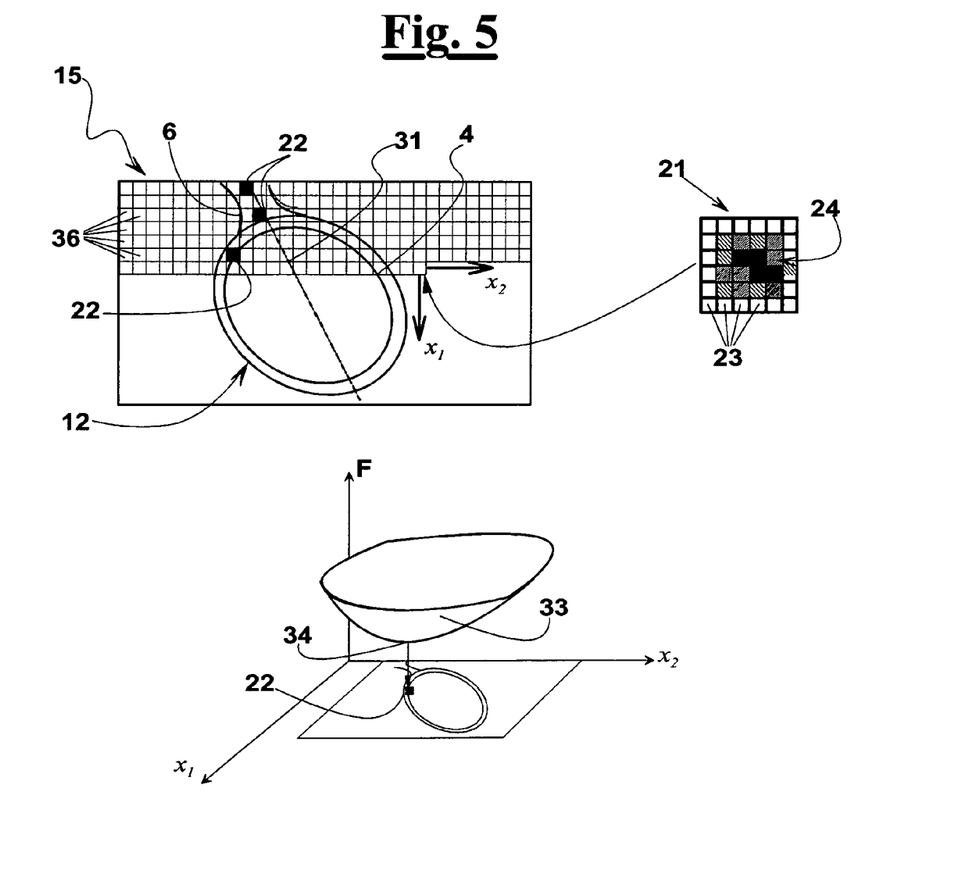
FIG. 5 diagrammatically shows the steps of scanning the ultrasound image of FIG. 4, by which previously defined anatomic points are retrieved.
Figure 6:
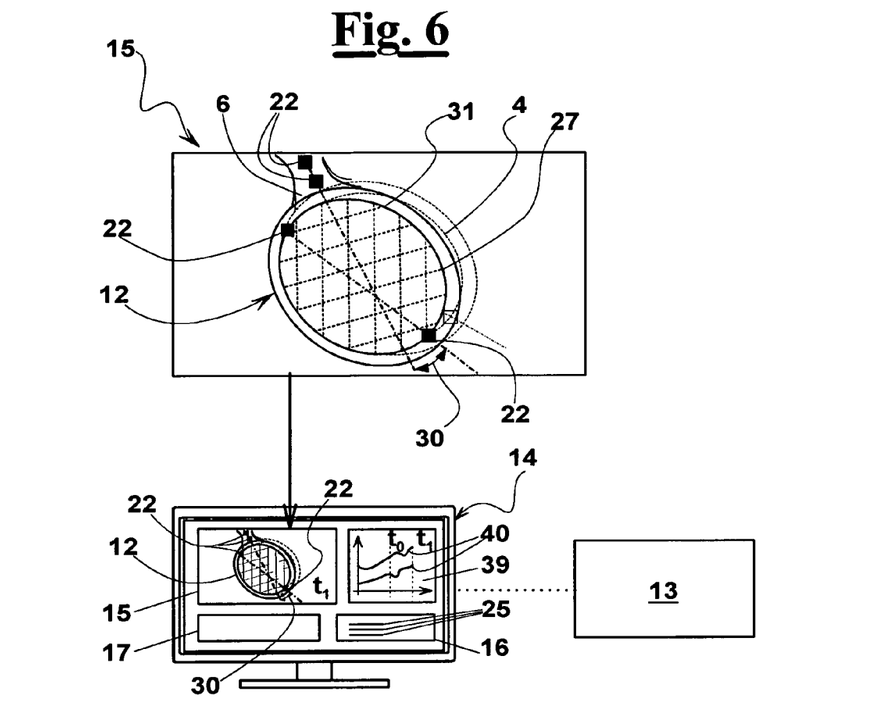
FIG. 6 shows the displaying unit of FIG. 2, where an ultrasound image is displayed subsequent to reference image.
Figure 7:
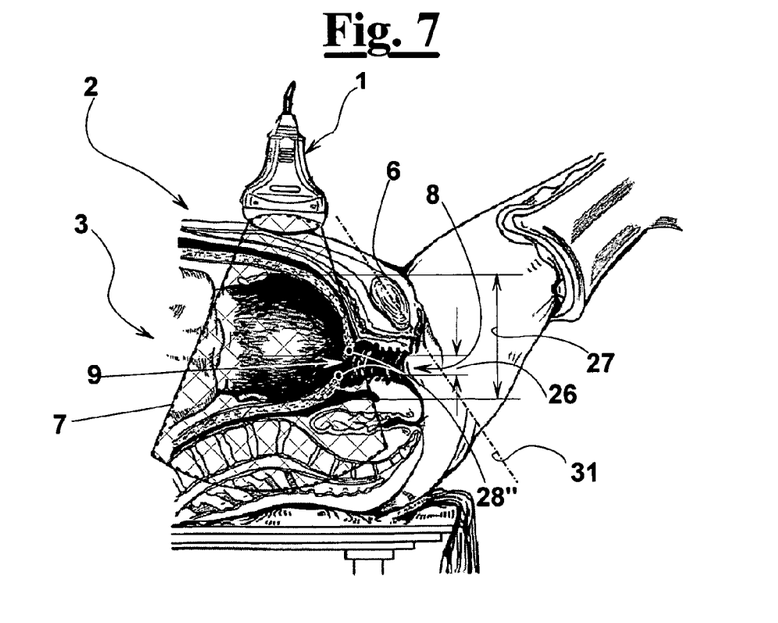
FIG. 7 represents more in detail a genital and reproductive apparatus of a parturient.

With reference to FIGS. 1 to 7, an apparatus 10 is described, according to the invention, for monitoring one or more morphological and physiological parameters that are related to the labor progress during childbirth. In a basic exemplary embodiment, the apparatus comprises an ultrasound probe 1, which is equipped with a means, not shown, for fixing the probe itself on the skin of a parturient 2 outside the upper ventral region or just below the sternum (FIG. 1), depending on the configuration that is actually most suitable for obtaining a satisfactory visualization of the desired portions of the woman's body and of the foetus 3. In the case displayed in FIG. 1, visual field 7 of ultrasound probe 1 includes substantially the whole foetus 3, in particular the head 4 as well as the whole endocervical canal 8 and a portion of the umbilical cord 5. As shown in FIG. 7, another possible suitable position of probe 1, is close to the pubis.

Figure 1:
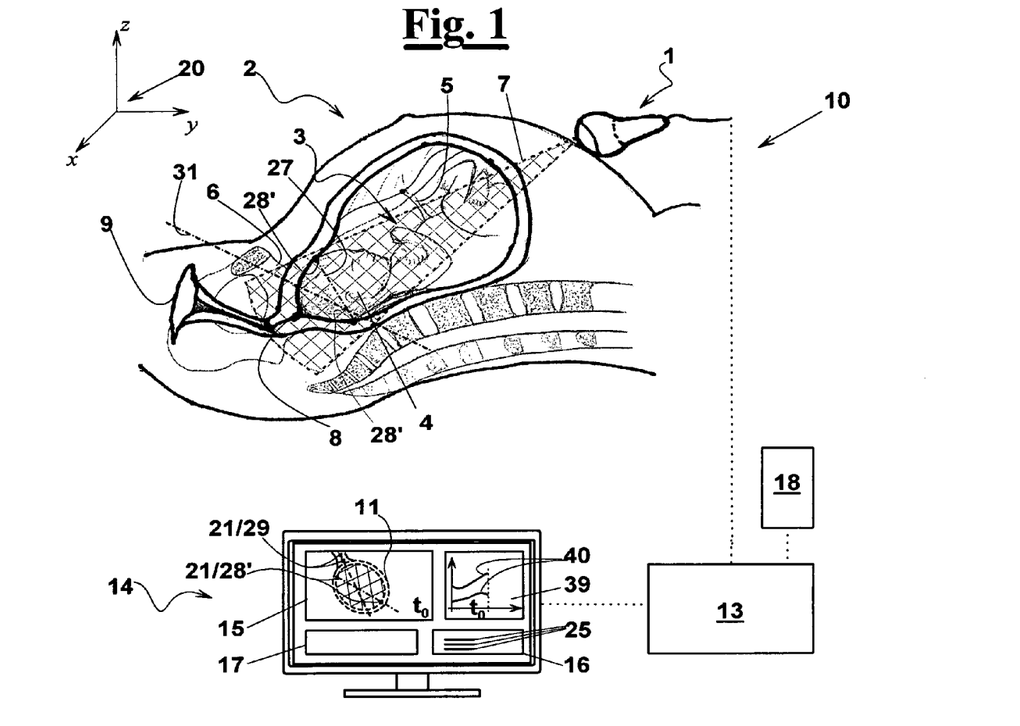
FIG. 1 is a schematic views of the apparatus according to the invention, for monitoring one or more morphological and physiological childbirth-related parameters, considered at different instants during the tracking of a parameter.
Figure 2:
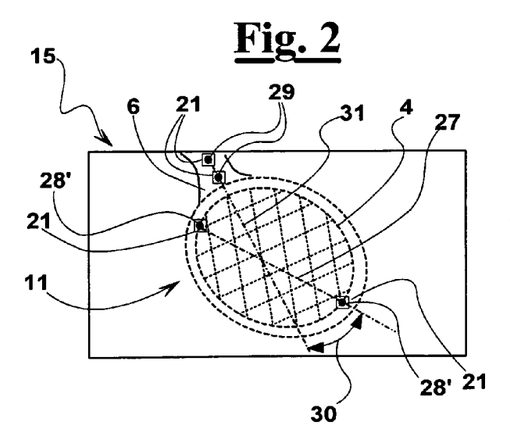
FIG. 2 shows more in detail the displaying unit 15 of the apparatus, along with a reference ultrasound image.
Figure 3:
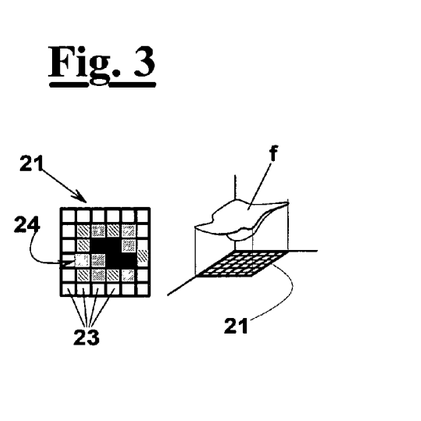
FIG. 3 diagrammatically shows a region of interest that is produced for identifying and tracking points on subsequent ultrasound images.

Ultrasound probe 1 is connected to a control unit 13 that provides an ultrasound image 11 on a displaying unit 15, substantially in real time $t_0$. In the exemplary embodiment, displaying unit 15 is integrated in an interactive graphic user interface 14 that comprises furthermore a device 16 for introducing the parameters 25 to be monitored; displaying unit 15, which is shown more in detail in FIG. 2, is used both for displaying ultrasound images 11 and for indicating the parameters 25 to be monitored by selecting anatomic reference points 28',28",29 directly on the reference ultrasound image 11. Graphic user interface 14 is also provided with a section 17 for displaying the numerical values of the selected parameters.

Figure 8:
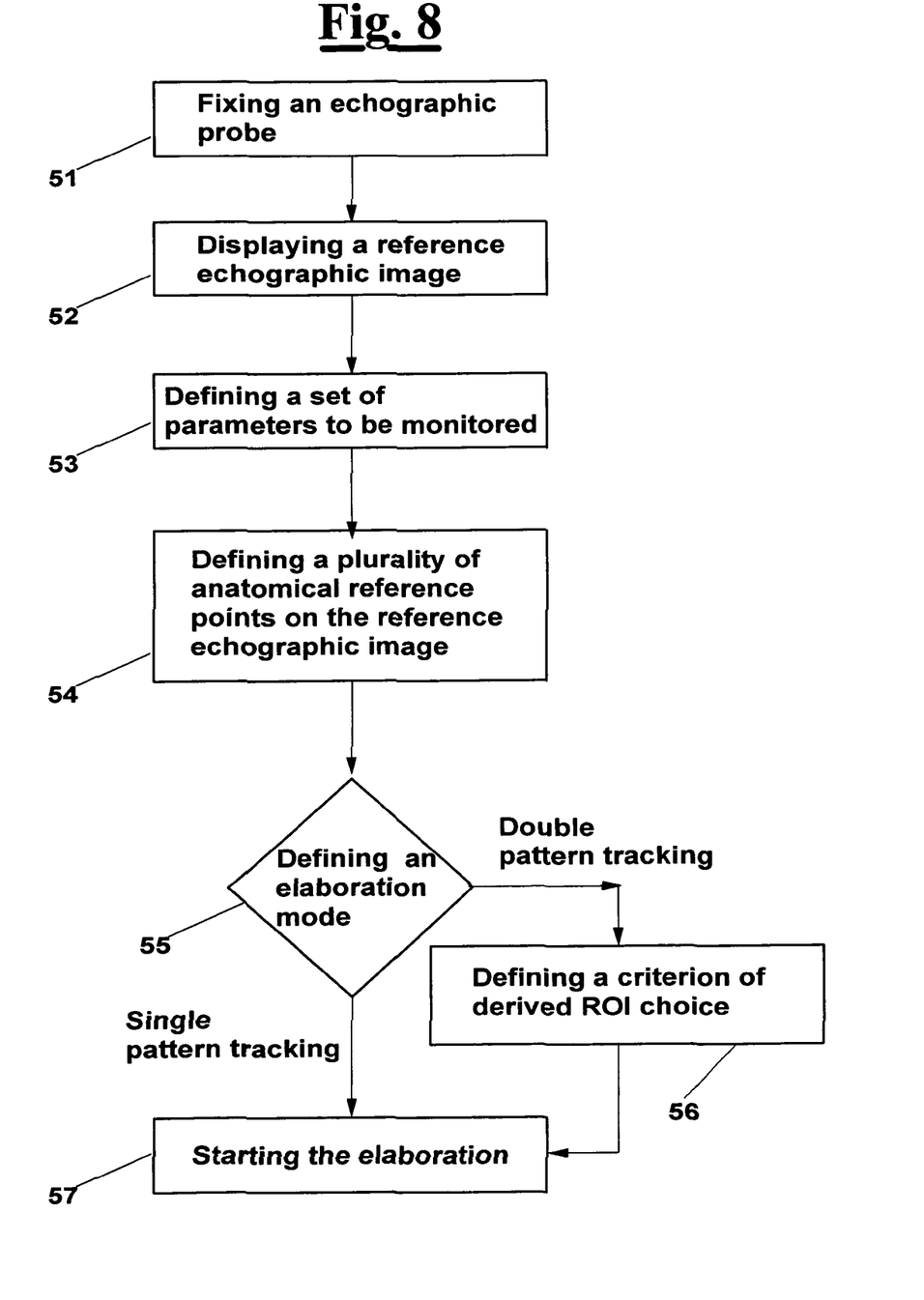
FIG. 8 is a block diagram that represents the steps to be performed by an operator who interacts with the apparatus according to the invention.

In order to monitor parameters 25, an operator interacts with apparatus 10, in particular with control unit 13, according to the steps of FIG. 8, which are referred to within parentheses.

The operator firstly fastens ultrasound probe 1 to the parturient's body 2 (51), in a position suitable for obtaining a satisfactory ultrasound image 11 (52) of the desired portions of the woman's body 2 and of foetus 3, as previously described.

Then, through device 16, the operator selects parameters 25 to be monitored during the next labor stages (53). Such parameters 25 may be selected, in particular among:
the dilation 26 of endocervical canal 8 (FIG. 7);
the length of endocervical canal 8;
the "foetal head station", i.e. the position of head 4 of foetus 3 with respect to a coordinate measured along the outlet path;
the "foetal head position" 30 (FIG. 2), i.e. the rotation of head 4 of foetus 3 with respect to a predetermined axis 31;
uterine contractions intensity, frequency, duration;
the position of one or more points of umbilical cord 5.

The operator selects, directly on reference ultrasound image 11 as displayed by screen 15, anatomic reference points 28',28" that are needed for real-time calculation of the value of each parameters 25 that have been selected (54). For example, for monitoring dilation 26 of endocervical canal 8, the operator selects a couple of points 28" on the edges 9 of the endocervical canal 8 (FIG. 7), or, preferably, a plurality of couples of points that are distributed along edges 9. In the case of the foetal head position 30, instead, the operator may select for instance a reference axis 31 integral with pelvis 6 of the parturient 2 and a couple of points 28' that identify biparietal diameter 27 of foetus 3 (FIGS. 1, 2 and 7), whose inclination with respect to reference axis 31 represents a rotation that is the above-mentioned foetal head position 30. Also in this case, this evaluation is preferably done in a redundant way, for instance by considering more than one couple of points 28'; in alternative to reference axis 31 integral with pelvis 6, the operator may choose a reference axis that is defined by a couple of points 28" that have been selected for monitoring dilation 26 of endocervical canal 8 (FIG. 7).

Through the above described technique of selection of anatomical reference points, the operator can define a parameter of interest, which may be different from the above-listed ones, provided that the new parameter can be expressed as a distance between two points or as a rotation angle of an axis with respect to a reference axis defined on foetus head or on parturient's body, for instance on parturient's pelvis 6. For the sake of conciseness, reference will be made only to the case of foetal head position 30, which is the only parameter shown through FIGS. 2-6, even if the apparatus is adapted to track a virtually unlimited plurality of parameters, provided that a suitable computing power is available.

Figure 9:
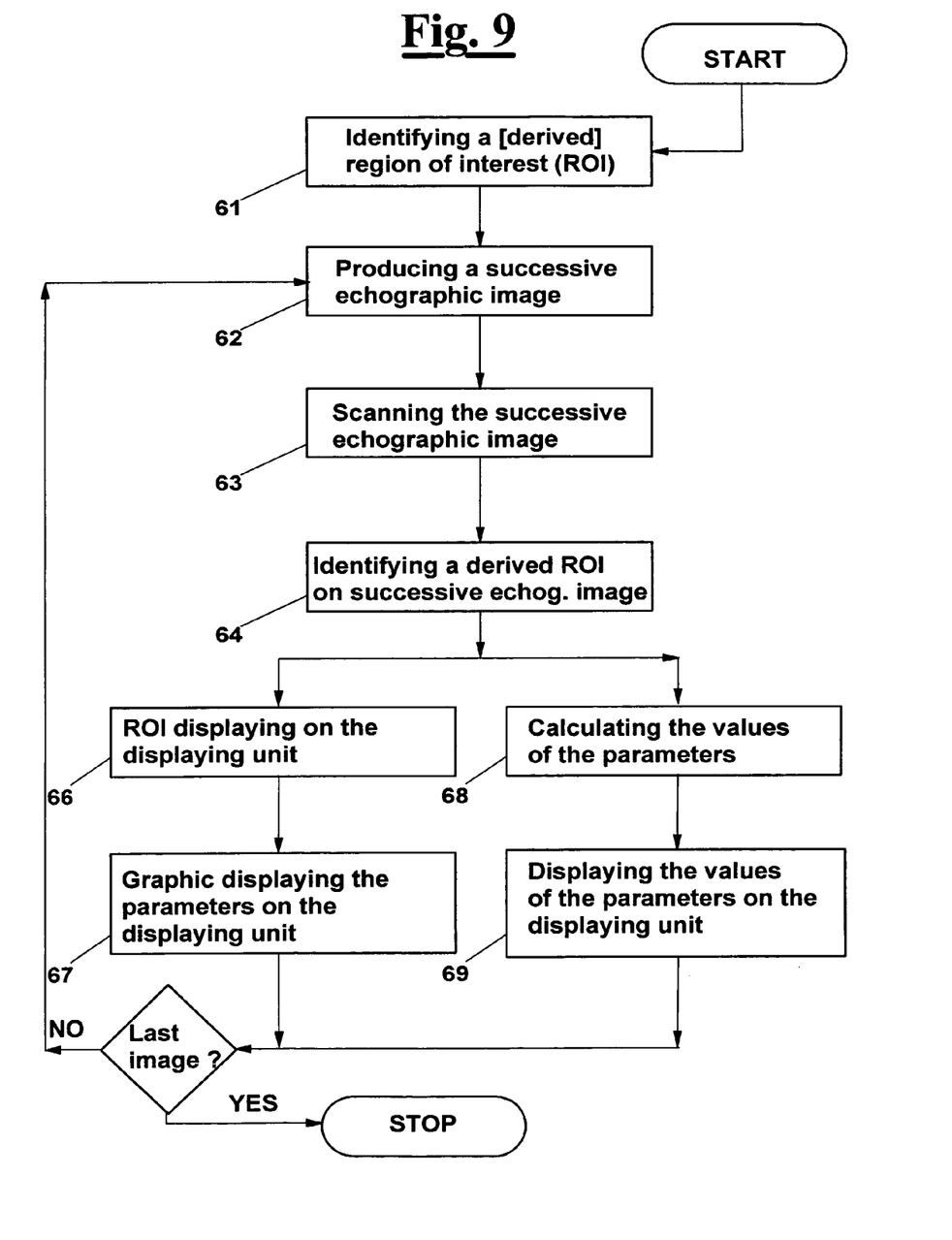
FIG. 9 is a block diagram of the method that is carried out by the algorithm-based program means that is resident in the control unit of the apparatus.

Once parameters 25 to be monitored, and respective anatomic reference points 28',28",29, have been selected, and options 55, 56, described hereinafter, have been fulfilled, the operator starts the elaboration (57), which is carried out by control unit 13 according to an algorithm-based program means that is resident in it. Control unit 13 works as described hereinafter, performing the steps of the block diagrams of FIG. 9, to which reference is made within parentheses.

The algorithm carries out a monitoring phase, or automatic "tracking", of specific "pixel patterns" through a sequence of consecutive ultrasound images. More in detail, and with reference to FIGS. 2 and 3, control unit 13 creates a region of interest (ROI) 21 about each reference point (61). Each ROI 21 has a prefixed size and comprises a set of pixels 23, which represents the pixel pattern 24 to be retrieved in the subsequent ultrasound images. For each pixel 23, the value of a prefixed local pixel function f is calculated. For example, the local pixel function f may associate a numerical value to a grey tonality of a pixel 23 in a grey scale, where the lowest/highest value is used for a white pixel and a highest/lowest value for a black pixel, respectively, or vice-versa.

Figure 4:
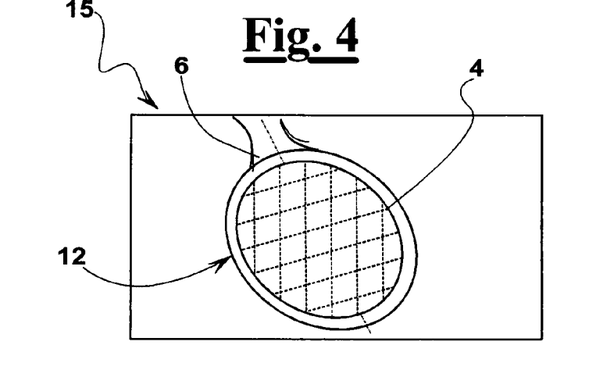
FIG. 4 shows a subsequent ultrasound image.

At a time $t_1$, control unit 13 defines an ultrasound image 12 (62; FIG. 4) that has been taken by the ultrasound probe, subsequent to reference image 11, in whose pixels the above mentioned reference function f is calculated; as shown in FIG. 5, control unit 13 carries out then a scanning step of subsequent image 12 (63), defining a plurality of domains 36 that have the same shape and size of ROI 21 (64), in order to track a group of pixels which has features that match the features of pixel pattern 24 as initially defined by the algorithm. To this purpose, and still by means of the resident algorithm, control unit 13 compares the set of the values calculated in ROI 21 with the values calculated in each domain 36, and finds out the domain 22 where the distribution of the values is the most similar to the distribution of the values calculated in ROI 21. The identified domain 36 is the domain where a predetermined object function F, or distance function, has a minimum value 34. For instance, according to a known method, the object function F may be the sum of the squares of the differences of values of the local pixel function f calculated for corresponding pixels in ROI 21 and in the domain 22. The coordinates $x_1,x_2$ of this recognized or tracked or derived ROI 22 are displayed substantially in real time on displaying unit 15 (66; FIG. 6), along with a line or a plurality of lines that represent the parameter of interest corresponding to selected groups of anatomic reference points (67), i.e. with simplified images of anatomic details, overlapped to the ultrasound current image. The anatomic detail may be, for example, the head of the foetus, together with such orientation parameters as foetal head position 30 or the inclination or the rotation with respect to the shoulders.

The computing means calculate then the distance and the angles of inclination that are needed for quantitatively expressing parameters 25, and the corresponding values are displayed in section 17 of displaying unit 15. Afterwards, the derived ROIs 22 that are retrieved in the subsequent image 12 are used in an iterative process, for recognizing the ROIs in further subsequent ultrasound images, not shown, up to the end of the session (70).

Parameter values 25 may furthermore be displayed as graphs 40 on a section 39 of graphic user interface 14 (68,69), in order to highlight their temporal evolution. Parameter values 25 may also be recorded in a mass memory unit 18, to be displayed in an off-line session. Anomalous parameter values and anomalous combinations of parameter values are advantageously saved in a separate memory device, preferably after being highlighted in a separate display unit or mode, not shown. The off-line consultation of the data recorded in mass memory unit 18 is useful, for instance, in case of doubts concerning a correct application of safety procedures and/or of good childbirth practice, in particular in case of unexpected complications that may have occurred during the childbirth.

In the above description, it has been assumed that the reference pixel patterns 24 to be tracked are identified in the initial image 11; however, for any anatomic reference point, in subsequent image 12 a pixel pattern 24 may be used which is identified in another ultrasound image, advantageously in an image that is produced immediately before image 12.

The algorithm will also offer the operator the option 55 (FIG. 8) of considering both types of pixel patterns, in order to maximize the accuracy in ROI recognition, at the expenses of some reduction in temporal resolution of the analysis. In this specific case, the operator will be also prompted to define the criterion (56) to be employed by control unit 13 to determine, in each elaborated image, the derived ROI 22 for each initially selected ROI 21. In fact, in this case, for each initial ROI 21 the algorithm will first provide two possible derived ROIs 22 as the result of two independent pattern trackings, and then a choice will be automatically made based on the operator-defined criterion. For instance, the position of each derived ROI 22 can be chosen as the average position between two alternatives that are provided by the algorithm, or it can be chosen as the position of the ROI that has the lowest object function F value 34 between the two values that are provided, or it can be chosen as the position that is closer to or farther from a determined range of possible "expected values", etc.

An external coordinate system 20 may be employed to correct, due, for instance to a parturient's movement. This way, any possible displacements of probe 1 can be taken into account, due for instance to an incidental movement of the parturient 2, starting from the control of the reference image up to the control of the subsequent images, and the position of ROI 21 of reference image 11 and of the corresponding derived ROIs 22 on subsequent images 12. To this purpose, (FIG. 1) an external or "absolute" coordinate system 20 may be provided, as well as a position sensor that can be associated to probe 1 and connected to control unit 13, in such a way that the absolute position of probe 1 with respect to coordinate system 20 is detected by control unit 13 that is provided with a summing means, which is adapted to sum the position of ROI 21 in the reference ultrasound image 11 and the position of the derived displaced ROI 12 with their corresponding positions in the fixed coordinate system 20. This way, a comparison is made between the positions of the ROIs 21,22 that takes into account the coordinate system 20 external to the parturient 2. The position sensor and the summing means may be easily implemented by a skilled person, therefore they are not described in detail here.

Notwithstanding reference has been made to pixels and local pixel functions, it is clear to a skilled person that they include both 2D and 3D pixels.

The foregoing description of a specific embodiment will so fully reveal the invention according to the conceptual point of view, such that others, by applying current knowledge, will be able to modify and/or adapt for various applications such embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. An apparatus for automatic electronic to measure of labor progress parameters during childbirth by ultrasound images obtained by ultrasonic pulses, said apparatus comprising:

an ultrasound probe attached onto a parturient's body and unmoved during said labor progress;

a fastening device to fasten said ultrasound probe onto a parturient's body so that said ultrasound probe has a visual field that includes a portion of a parturient's body and of a fetus, said parturient's endocervical canal or a parturient's pubis;

a control unit receives and analyzes signals from said ultrasound probe, said control unit creates or receives as input by said probe a reference ultrasound image and a plurality of subsequent ultrasound images, which are taken in succession of time after said reference ultrasound image;

a graphic user interface to display said ultrasound image and said plurality of subsequent ultrasound images; said graphic user interface allows a selection of a region of interest within said reference ultrasound image by an operator, wherein said region of interest is substantially centered about said portion of a parturient's body, said region of interest comprising a plurality of pixels; and wherein said graphic user interface displays labor parameters overlapping an ultrasound image;

wherein said control unit comprises:

an automatic tracking system tracks said region of interest, said automatic tracking system identifies derived regions of interest within selected images of said plurality of subsequent ultrasound images, said derived regions of interest deriving from said region of interest that is selected within said reference ultrasound image, said automatic tracking system comprising:

software logic calculates a predetermined local pixel function (f) for each pixel or group of pixels of said region of interest in said reference ultrasound image and in each selected image of said plurality of subsequent ultrasound images, software logic iteratively calculates, starting from said reference ultrasound image, a position of said derived region of interest in each selected image, said software logic iteratively calculates is programmed to perform comparisons between:

values of said local pixel function (f) calculated at the pixels of said region of interest of an image of the selected images;

values of said local pixel function calculated at the pixels of said region of interest of a subsequent ultrasound image;

software logic compares each position of said derived region of interest with the position of said region of interest in said reference ultrasound image or in another image of said selected images and calculates a labor progress parameter;

and wherein said software logic iteratively calculates positions of said derived region of interest comprises:
   a software logic for calculating said local pixel function (f) within a plurality of domains of said subsequent ultrasound images;
   a software logic calculates a predetermined object function (F) in each of said domains, said object function associates to each of said domains a deviation value between said local pixel function (f) as calculated in said domain and said local pixel function (f) as calculated in said region of interest;
   a software logic determines a derived region of interest of a subsequent ultrasound image in which said object function (F) has a minimum value;
and wherein said tracking system allows to track substantially in real time and with a predetermined level of accuracy, before and during childbirth, one or a plurality of physiological labor parameters related a childbirth progress;
and wherein said local pixel function (f) has a number associated to a pixel and is related to a grey tonality of a grey scale or is deduced by a radio-frequency spectral analysis of an ultrasound image; wherein a lowest/highest value is used for a white pixel and a highest/lowest value is used for a black pixel, respectively or vice-versa;
and wherein said apparatus is designed to interface and integrate with available ultrasound instruments;
and wherein said operator, using said graphic user interface, can select labor parameters to be automatically monitored, in conjunction with a parturient's anatomic reference point, said selectable labor parameters are:
uterine contraction intensity and frequency,
fetal cardiac frequency,
endocervical canal dilation,
endocervical canal length,
fetal head station, which is the position of a head of a fetus with respect to a coordinate measured along said parturient's endocervical canal;
distance of a fetal head from a parturient's anatomical references,
fetal head rotation,
one or more points of umbilical cord position,
fetus position before and during a fetus' descent through a parturient's endocervical canal,
physiological parameters of a parturient and of a fetus; and variations in time of said physiological parameters;
and wherein said operator, using said graphic user interface, can select additional labor parameters of interest provided that said parameters can be expressed as a distance between two points or as a rotation angle of an axis with respect to a reference axis defined on a fetus head or on a parturient's body;
and wherein said labor parameters, combined with said reference ultrasound image and said plurality of subsequent ultrasound images enable a medical team to evaluate on an objective basis whether a Cesarean section is necessary and to support such a necessity with a documentary evidence of a need of such a practice.

2. An apparatus according to claim 1, wherein said control unit select a further region of interest that is substantially centered about said portion of said parturient' body; said labor progress parameters during childbirth defined by a combination of said region of interest and of said further region of interest; and wherein said labor progress parameters are independent from movements and positions of said parturient's body which can assume a desired position during a childbirth's progress, said position is selected from a group consisting of standing, sitting or lying-down positions.

3. An apparatus according to claim 1, wherein said graphic user interface is designed to provide an operator an option of selecting a further reference ultrasound image among one of said subsequent ultrasound images, such that a first tracking and a second tracking on two pluralities of pixels are carried out concurrently; and wherein said user's interface software logic is programmed to iteratively calculate and to perform the steps of:
   electronically compares values of said local pixel function (f) calculated at pixels of said region of interest of said reference ultrasound image, and values of said local pixel function (f) calculated at pixels of said derived region of interest of a subsequent ultrasound image, such that a first position of said derived region of interest is identified;
   electronically compares between values of said local pixel function (f) calculated at pixels of said further reference image, and values of said local pixel function (f) calculated at pixels of said region of interest of a subsequent ultrasound image, such that a second position of said derived region of interest is identified;
   electronically identifies a further derived region of interest through a comparison between tracking of a first position and tracking of said second positions of said derived region of interest according to prefixed selectable criteria;
   and wherein said tracking of a first position allows to take into maximum account any possible change of tissues during the childbirth, whereas said tracking of a second position allows to eliminate extraneous elements that may affect a calculation of said derived region of interest;
   and wherein said operator has the option to select an elaboration mode between a single or double type of pixel pattern tracking to maximize the accuracy of a region of interest recognition.

4. An apparatus according to claim 3, wherein said graphic user interface is designed to provide an operator an option of selecting a selectable prefixed criterion from criteria selected from a group consisting of:
   a position that is identified by a lowest object function (F) value;
   the position that is closer to a predetermined set of values;
   the position that is farther from a predetermined set of values;
   an average position between said first and said second position;
   and wherein said object function (F) is a sum of the squares of the differences of values of the local pixel function (f) calculated for corresponding pixels in a region of interest and in a derived region of interest;
   and wherein said graphic user interface is able to display a simplified image of:
   the position of a parturient's genitals,
   of a parturient's reproductive system,
   a parturient's fetus,
   to evaluate a progression stage and a correct evolution of a childbirth procedure.

5. An apparatus according to claim 1, wherein said control unit comprises software logic to measure an absolute position of said ultrasound probe with respect to a coordinate system external to said parturient, and wherein said control unit has software logic to receive said position parameter; and said software logic is programmed to sum said position parameter and the position of said derived region of interest with respect to said ultrasound probe, such that said software logic to perform a comparison between an actual position of said regions of interest taking into account said coordinate system external to said parturient's body;

and wherein an alignment is possible between said position of said region of interest in a reference image, and of the corresponding regions of interest on the subsequent images, and an univocal coordinate system, external to a parturient's body, in particular a fixed coordinate system, in order to take into account movements of a parturient's body during a childbirth, more precisely during the time said reference image is taken until subsequent images are processed.

6. An apparatus according to claim 1, wherein said graphic user interface is designed define as input a plurality of regions of interest selected by an operator within said reference ultrasound image, each region of interest defines a same labor progress parameter;

and wherein said regions of interest may be used to automatically track one of moving portions of an ultrasound image that follows in time a reference ultrasound image, in terms of position with respect to a portion of a parturient's body that remains substantially fixed during a childbirth.

7. An apparatus according to claim 1, wherein said labor progress parameter, associated to a fetus descent along an outlet path through said endocervical canal, is defined by a region of interest selected from a group consisting of:

a dilation of said parturient's endocervical canal,
a position of the head of said fetus;
the rotation of the head of said fetus;
and wherein said dilation, is associated to a distance between at least one couple of regions of interest selected on a edge of said endocervical canal; and wherein the length of a parturient's endocervical canal is computed to compare the dilation of the upper part a parturient's cervical canal with the dilation of the lower part of a parturient's cervical canal;
and wherein said position of the head of said fetus is associated with a region of interest that is selected on a fixed portion of said parturient's body and with a region of interest that is selected on the head of said fetus;
and wherein said rotation of the head of said fetus is identified by the fetal head position, said rotation associated with an angle that is formed by a line that is defined by two regions of interest centered on a fixed anatomic portion of said body of said parturient and by a line that is defined by two regions of interest integral to said fetus;
and wherein said progress parameters may be displayed as graphs on said graphic user interface to highlight their temporal evolution.

8. An apparatus according to claim 1, wherein said reference ultrasound image and said subsequent ultrasound images are images of any cross sectional plane of said visual field selected by an operator.

9. An apparatus according to claim 1, wherein said region of interest is a region of a three-dimensional space, defines a three-dimensional region, obtained as an union of two-dimensional regions of interest of a plurality of ultrasound images of plane sections of said visual field, said plurality of ultrasound images is obtained by rotating said visual field around an axis common to said plane sections.

10. An apparatus according to claim 1, wherein said region of interest is a region of a three-dimensional space, in particular, obtained directly through a 3D real time acquisition.

11. An apparatus according to claim 1, wherein said plurality of subsequent images in which said derived region of interest is identified by sampling at a predetermined frequency.

12. An apparatus according to claim 1, wherein said position of the head of a fetus is associated with a further derived region of interest that is selected on a fixed portion of said parturient's body and with a further derived region of interest that is selected at the head of said fetus.

13. An apparatus according to claim 1, wherein said graphic user interface provides a software logic to signal an anomalous value of a labor progress parameter or a fetus physiological parameter with respect to a predetermined range, or an anomalous combination of a plurality of labor progress parameters or of fetus physiological parameters.

14. An apparatus according to claim 1, further comprising a memory component to store values of said labor progress parameters, comprising anomalous values and anomalous combination of values; and wherein said memory component can be accessed by an off-line consultation to produce a childbirth history in case of doubts concerning a correct application of a safety procedure or a of a good childbirth practice by a medical personnel, in case of unexpected complications that may have occurred during a childbirth procedure.

* * * * *